United States Patent
Ferreyrol

(10) Patent No.: US 7,520,903 B2
(45) Date of Patent: Apr. 21, 2009

(54) ENDOPROSTHESIS WITH PROJECTIONS FOR DELIVERING ACTIVE AGENTS

(75) Inventor: Bruno Ferreyrol, Roquefort-la-Bedoule (FR)

(73) Assignee: Novatech SA, La Ciotat (FR)

( * ) Notice: Subject to any disclaimer, the term of this patent is extended or adjusted under 35 U.S.C. 154(b) by 178 days.

(21) Appl. No.: 11/328,111

(22) Filed: Jan. 10, 2006

(65) Prior Publication Data

US 2006/0161264 A1 Jul. 20, 2006

(30) Foreign Application Priority Data

Jan. 18, 2005 (FR) .................................. 05 00500

(51) Int. Cl.
*A61F 2/06* (2006.01)
(52) U.S. Cl. ................... 623/23.7; 623/23.64; 623/1.15
(58) Field of Classification Search ....... 623/1.11–1.35; 604/96, 101
See application file for complete search history.

(56) References Cited

U.S. PATENT DOCUMENTS

| | | | |
|---|---|---|---|
| 5,236,446 A * | 8/1993 | Dumon ....................... 623/6.16 |
| 5,242,397 A * | 9/1993 | Barath et al. ............ 604/103.01 |
| 6,210,392 B1 | 4/2001 | Vigil et al. |
| 6,245,076 B1 * | 6/2001 | Yan ............................. 606/108 |
| 6,254,632 B1 | 7/2001 | Wu et al. |
| 6,379,381 B1 * | 4/2002 | Hossainy et al. ........... 623/1.42 |
| 6,506,437 B1 | 1/2003 | Harish et al. |
| 6,641,607 B1 | 11/2003 | Hossainy et al. |
| 6,695,830 B2 * | 2/2004 | Vigil et al. .................. 604/509 |
| 6,942,680 B2 * | 9/2005 | Grayzel et al. .............. 606/194 |
| 2002/0082679 A1 | 6/2002 | Sirhan et al. |
| 2005/0230039 A1 * | 10/2005 | Austin et al. ............. 156/272.8 |
| 2007/0088427 A1 * | 4/2007 | Ozdil et al. ................ 623/1.16 |

FOREIGN PATENT DOCUMENTS

| | | |
|---|---|---|
| EP | 1393766 A1 | 3/2004 |
| WO | 0147451 | 7/2001 |
| WO | 0167991 | 9/2001 |

OTHER PUBLICATIONS

Preliminary Search Report dated Sep. 12, 2005.

* cited by examiner

*Primary Examiner*—Suzette J Gherbi
(74) *Attorney, Agent, or Firm*—Dickinson Wright, PLLC

(57) ABSTRACT

An endoprosthesis may be implanted in the region of an anatomical canal that is experiencing impairment. An exterior surface wall of the endoprosthesis bears projecting studs that cooperate with the wall of the anatomical canal so as to hold the endoprosthesis in position. One of the projecting studs is hollow and acts as a reservoir for a product that is active against the impairment.

5 Claims, 1 Drawing Sheet

ENDOPROSTHESIS WITH PROJECTIONS FOR DELIVERING ACTIVE AGENTS

BACKGROUND OF THE INVENTION AND DESCRIPTION OF THE PRIOR ART

The present invention relates to an endoprosthesis for an anatomical canal, which is intended to be implanted inside an anatomical canal, in a region of this canal that is experiencing impairment and of which the exterior surface of the wall bears projecting studs intended to collaborate with the wall of said anatomical canal in order to hold said endoprosthesis in position therein.

Such an impairment may be an affliction, such as a stenosis or a collapsus, leading to narrowing of said anatomical canal and combated, in the known way, using an implanted endoprosthesis when the reduction in the diameter of said canal is significant, for example greater than 50%. This endoprosthesis holds the passage of said canal open at said region, allowing fluids to circulate through it. Such an endoprosthesis acts essentially as a mechanical stent.

It is also known that implanting such an endoprosthesis for holding a passage open is generally associated with suitable medical treatment, such as the administration of anti-inflammatory drugs, of radiotherapy, of chemotherapy, etc. Now, this medical treatment is applied in a general way to the patient, that is to say anally, orally or in a drip in the case of drugs and chemical products and by irradiation through the patient's body in the case of radiotherapy. The result of this is that the doses applied to the patient are very much higher than the doses found at the region where the prosthesis is implanted, which means that one or other of the following situations arises:

either there is a desire for the patient not to be subjected to an excessively strong overall treatment, which means that the doses of the treatment at said implantation region are very much lower than they need to be in order to effectively combat said narrowing;

or there is a desire for the doses at the implantation region to be medically effective, which means that the patient is then subjected to very high generalized doses which may prove detrimental to his health.

Apart from stenosis and collapsus recalled hereinabove, an anatomical canal may suffer other impairments, such as lesions, infections, inflammations, irritations, hypersensitivities, etc. The latter impairments, which hitherto did not lead to the use of an endoprosthesis, require medical treatment which, as mentioned hereinabove with regard to stenosis and collapsus, is applied in the general manner to the patient, with the same disadvantages.

Hence the object of the present invention is to remedy these disadvantages, whatever the type of impairment to the anatomical canal.

SUMMARY OF THE INVENTION

To this end, according to the invention, the endoprosthesis for an anatomical canal, which is intended to be implanted in a region of this canal that is experiencing impairment and of which the exterior surface of the wall bears projecting studs intended to collaborate with the wall of said anatomical canal in order to hold said endoprosthesis in position therein, is notable in that at least one of said projecting studs is hollow and acts as a reservoir able to contain a product that is active against said impairment and to allow said active product to act against this impairment.

First, said endoprosthesis delivers said active product to the very site of the impaired region of the anatomical canal. This active product may therefore be dosed suitably and appropriately with respect to the treatment to be carried out in this region.

The endoprosthesis according to the present invention therefore constitutes a main or complementary means of treating the impairment to the anatomical canal. In the instance whereby, hitherto, the impairment (lesion, infection, inflammation, irritation, hypersensitivity, etc.) does not call for the implantation of an endoprosthesis, the endoprosthesis according to the invention has the specific objective of delivering the active product in situ. By contrast, when the impairment (stenosis, collapsus) entails the use of a mechanical stent, the endoprosthesis according to the invention may be the result of an endoprosthesis already in existence and improved to incorporate therein at least one reservoir of active product: the endoprosthesis thus improved therefore is able simultaneously to act as a mechanical stent in the anatomical canal and to deliver the active product.

The present invention therefore relates, on the one hand, to entirely novel endoprostheses suited to the treatment of impairments for which no endoprosthesis has yet been used and, on the other hand, to known endoprostheses improved to allow at least one active product to be delivered in situ.

The endoprosthesis according to the present invention may, once said active product has been exhausted, be refilled endoscopically or replaced by another suitably filled with active product.

When said active product is a radioactive isotope, each hollow stud containing said radioactive product may be plugged by a sealed stopper and form a reservoir sealed against said product, only the radioactive radiation of which passes toward said impairment. By contrast, each hollow stud containing said radioactive product may be plugged by a stopper exhibiting permeability to said radioactive product and allowing the latter to permeate in a controlled manner toward said impairment.

If the active product is chemical or pharmaceutical, each hollow stud containing said active product is plugged by a stopper exhibiting controlled permeability to said active product and allowing the latter to permeate in a controlled manner toward said impairment.

In addition to the hollow stud or studs serving as a reservoir of active product, it is advantageous for the endoprosthesis according to the invention to comprise at least one other hollow stud to contain a radiopaque product able to serve to locate said endoprosthesis within said anatomical canal.

Such an endoprosthesis may further comprise, in addition to the hollow studs to serve as a reservoir of active product and to contain a radiopaque product, at least one other stud containing a pellet, for example made of pure gold, acting as a marker.

In a special case where said studs of the endoprosthesis form lines—for example longitudinal lines distributed around said endoprosthesis with the studs in two adjacent lines staggered relative to one another—it is advantageous, within such a line, for one stud to contain said marker pellet while all the other studs of said longitudinal line contain said radiopaque product.

DESCRIPTION OF THE DRAWINGS

The figures of the attached drawing will make it easier to understand how the invention may be embodied. In these figures, identical references denote similar elements.

DESCRIPTION OF THE PREFERRED EMBODIMENT

Figure 1:
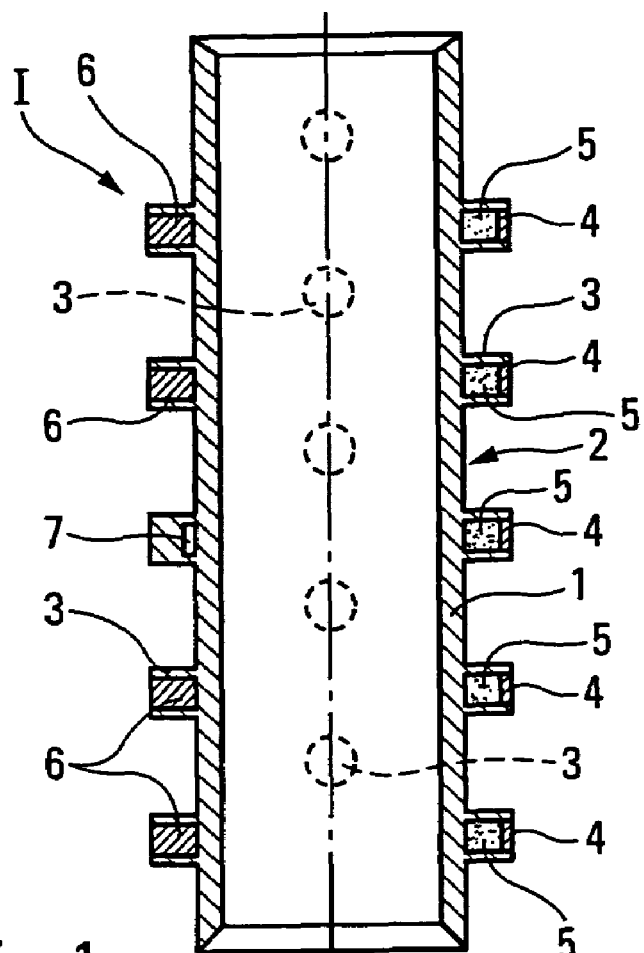
FIG. 1 illustrates, in longitudinal axis section, one exemplary embodiment of the endoprosthesis according to the present invention.
Figure 2:
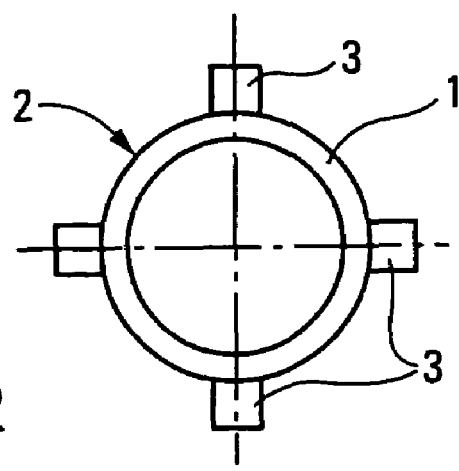
FIG. 2 is a view from above of the endoprosthesis of FIG. 1.

The tubular endoprosthesis I according to the present invention as shown in FIGS. 1 and 2 can be made of any flexible, semi-rigid or rigid material, that may or may not be reinforced by an internal framework, able to be well-tolerated by the patient's organ in which it is to be implanted. However, for preference, it is made of a silicone-based elastomer that exhibits good elastic deformation properties.

For the purposes of clarity, the tubular endoprosthesis I depicted is formed of a straight tube portion and is able to form a tracheal or bronchial endoprosthesis. However, it is quite obvious that the present invention also relates to tubular endoprosthesis of more complicated shapes, for example curved, Diablo-shaped or Y-shaped prostheses such as are required, for example, for trachea-bronchial endoprostheses. In general, the endoprosthesis according to the present invention is tailored, in shape and in diameter, to the canals in which it is to be implanted.

The endoprosthesis I shown by way of example in FIGS. 1 and 2 is of the type described in document U.S. Pat. No. 5,236,446. It comprises a tubular body 1 the exterior surface of the wall 2 of which bears a plurality of studs 3 distributed in longitudinal lines and spaced apart in the longitudinal direction and in the peripheral direction and intended to collaborate with the wall of the implantation canal in order to hold said endoprosthesis in position. The ends of the tubular body 1 are open and internally chamfered.

In accordance with the present invention, at least some of the studs 3 are hollow and plugged by stoppers 4. Thus, each of these hollow studs 3 can serve as a reservoir able to contain an active product 5 that is active against the impairment, at the site of which the endoprosthesis I will be implanted. When the active product 5 is a radioactive isotope working by radiation, the stoppers 5 of the corresponding studs 3 are either porous to allow the product to permeate in a controlled manner or impervious so as to allow only the radioactive radiation to pass. When the active product 5 is a drug or chemical substance, the stoppers 4 of the corresponding studs 3 are of the osmotic membrane type and have controlled permeability suited to the characteristics of the drug or of this chemical substance, such as their molecule size, viscosity, etc.

Furthermore, other hollow studs 3 are filled with a radiopaque material 6, for example a silicone filled with barium sulfate and serving to locate the endoprosthesis I in the implantation canal by means of X-ray.

In addition, one hollow or solid stud 3 may contain a pure gold pellet 7 which acts as a signature for the endoprosthesis I.

In the example of FIG. 1, a complete longitudinal line of studs 3 bears the opaque substance 6, except for the central stud 3 that contains the pure gold pellet 7.

The invention claimed is:

1. An endoprosthesis for an anatomical canal, which is intended to be implanted in a region of said anatomical canal that is experiencing impairment, said endoprosthesis comprising a body having a wall including an exterior surface that includes individual projecting studs for collaborating with the wall of said anatomical canal in order to hold said endoprosthesis in position therein, said projecting studs being distributed in longitudinal lines and spaced apart in the longitudinal direction and in the peripheral direction, wherein:
    at least some projecting studs of a longitudinal line are hollow and contain a radiopaque product,
    at least some of the other studs are hollow and act as a reservoir for containing a not radiopaque product that is active against said impairment and for allowing said active product to act against this impairment, and
    at least one projecting stud, of the longitudinal line comprising the hollow projecting studs containing a radiopaque product, contains a pellet acting as a signature for said endoprosthesis.

2. The endoprosthesis as claimed in claim 1 able to be used with an active product of the radioactive type, wherein each hollow stud containing said radioactive product is plugged by a sealed stopper to seal said reservoir against said product such that only the radioactive radiation of said product passes toward said impairment.

3. The endoprosthesis as claimed in claim 1 able to be used with an active product of radioactive type, wherein each hollow stud containing said radioactive product is plugged by a stopper exhibiting permeability to said radioactive product and allowing said radioactive product to permeate said stopper in a controlled manner toward said impairment.

4. The endoprosthesis as claimed in claim 1 able to be used with an active product of chemical or pharmaceutical type, wherein each hollow stud containing said active product is plugged by a stopper exhibiting controlled permeability to said active product and allowing said active product to permeate said stopper in a controlled manner toward said impairment.

5. The endoprosthesis as claimed in claim 1, wherein said longitudinal line comprises one projecting stud with said pellet while the other studs of said line contain said radiopaque product.

* * * * *